US011780590B2

(12) United States Patent
Michalakos et al.

(10) Patent No.: US 11,780,590 B2
(45) Date of Patent: Oct. 10, 2023

(54) AIRCRAFT CABIN DISINFECTION

(71) Applicant: Honeywell International Inc., Charlotte, NC (US)

(72) Inventors: Peter M. Michalakos, Arlington Heigtits, IL (US); Amanda Childers, Arlington Heigtits, IL (US); Giorgio C. Isella, Culver City, CA (US); Tim Lippold, Huntington Beach, CA (US); Sean Skomurski, Highland Park, IL (US)

(73) Assignee: Honeywell International Inc., Charlotte, NC (US)

( * ) Notice: Subject to any disclaimer, the term of this patent is extended or adjusted under 35 U.S.C. 154(b) by 365 days.

(21) Appl. No.: 16/949,453

(22) Filed: Oct. 29, 2020

(65) Prior Publication Data
US 2022/0048633 A1    Feb. 17, 2022

Related U.S. Application Data (60) Provisional application No. 63/066,135, filed on Aug. 14, 2020.

(51) Int. Cl.
*B64D 13/06* (2006.01)
*A61L 2/22* (2006.01)

(52) U.S. Cl.
CPC ............... *B64D 13/06* (2013.01); *A61L 2/22* (2013.01); *A61L 2202/15* (2013.01);
(Continued)

(58) Field of Classification Search
CPC .... A61L 2/22; A61L 2202/15; A61L 2202/25; A61L 9/015; A61L 9/14; A61L 2209/11;
(Continued)

(56) References Cited

U.S. PATENT DOCUMENTS 3,436,039 A * 4/1969 Emmons ............... B64D 13/02
                                                244/129.5
4,886,657 A * 12/1989 Ratcliff ................ A01N 59/00
                                                424/53
(Continued)

FOREIGN PATENT DOCUMENTS

| CA | 2540948 A1 | 9/2007 |
| EP | 2777716 A1 | 9/2014 |
| WO | 2017205418 A1 | 11/2017 |

OTHER PUBLICATIONS

Clordisys, "Material Compatibility", May 12, 2018 (Year: 2018).*
(Continued)

*Primary Examiner* — Jennifer Wecker
*Assistant Examiner* — Brady C Pilsbury
(74) *Attorney, Agent, or Firm* — Shumaker & Sieffert, P.A.

(57) ABSTRACT

The disclosure describes a method for disinfecting an aircraft cabin that includes injecting a non-peroxide disinfectant into an environmental control system of an aircraft and discharging cabin supply air through the environmental control system to discharge the non-peroxide disinfectant into the aircraft cabin. In some instances, the method includes aerosolizing the disinfectant into a plurality of liquid droplets while injecting the disinfectant into the environmental control system. In some instances, the injected disinfectant includes a non-corrosive, non-toxic disinfectant, such that the disinfectant may be discharged into the aircraft cabin in the presence of personnel in the aircraft cabin.

19 Claims, 4 Drawing Sheets

(52) U.S. Cl.
CPC ... *A61L 2202/25* (2013.01); *B64D 2013/0651* (2013.01); *B64D 2013/0688* (2013.01)

(58) Field of Classification Search
CPC ............. A61L 2209/16; A61L 2209/21; A61L 2209/211; A61L 2209/212; B64D 2013/0651; B64D 2013/0688; B64D 2013/0625; B64F 5/30
See application file for complete search history.

(56) References Cited

U.S. PATENT DOCUMENTS

| | | | | |
|---|---|---|---|---|
| 2004/0265459 | A1* | 12/2004 | Lark | A01N 59/00 426/532 |
| 2005/0053515 | A1* | 3/2005 | Yates | A61L 9/16 422/4 |
| 2005/0074359 | A1 | 4/2005 | Krieger et al. | |
| 2005/0260138 | A1* | 11/2005 | Flanigan | A61L 9/03 424/45 |
| 2016/0214723 | A1* | 7/2016 | Fox | B64D 13/06 |
| 2016/0214724 | A1* | 7/2016 | Fox | B01D 53/30 |

OTHER PUBLICATIONS

Akzo Nobel, "Safety Data Sheet: Chlorine Dioxide Aqueous Solution, ClO2 <3%", Revised May 2000 (Year: 2000).*

Baron, "Generation and Behavior of Airborne Particles (Aerosols)," National Institute for Occupational Safety and Health Centers for Disease Control and Prevention, 40 pp.. Applicant points out, in accordance with MPEP 609.04(a), that the year of publication, 2006, is sufficiently earlier than the effective U.S. filing date, so that the particular month of publication is not in issue.
"Hydrogen Peroxide Material Compatibility Chart," Is MED Specialties, Jul. 9, 2020, 3 pp.
Elmaghraby et al., "Ventilation strategies and air quality management in passenger aircraft cabins: A review of experimental approaches and numerical simulations," Science and Technology for the Built Environment, Oct. 30, 2017, 17 pp.
Bagshaw et al., "The Aircraft Cabin Environment—Chapter 47," Elsevier, Science Direct, Travel Medicine (Four Edition), p. 409-436, Applicant points out, in accordance with MPEP 609.04(a), that the year of publication, 2019, is sufficiently earlier than the effective U.S. filing date, so that the particular month of publication is not in issue.
Extended Search Report from counterpart European Application No. 21189739.2 dated Jan. 12, 2022, 8 pp.
Response to Extended Search Report dated Jan. 12, 2022, from counterpart European Application No. 21189739.2, filed Feb. 21, 2022, 36 pp.
Notice of Intent to Grant and Text Intended to Grant from counterpart European Application No. 21189739.2 dated Jan. 4, 2023, 37 pp.

* cited by examiner

AIRCRAFT CABIN DISINFECTION

This application claims the benefit of U.S. Provisional application No. 63/066,135, entitled "AIRCRAFT CABIN DISINFECTION" and filed on Aug. 14, 2020, which is incorporated herein by reference in its entirety.

TECHNICAL FIELD

The present disclosure relates to systems and techniques for aircraft cabin disinfection.

BACKGROUND

Outbreaks of infectious diseases, such as SARS, MERS, and COVID-19, may create a public perception of increased risk of infection through airline travel, resulting in reduced demand for airline travel by commercial airline passengers. To further increase sanitation of an aircraft cabin and improve confidence of commercial airline passengers, airlines may manually wipe or spray high-touch surfaces with liquid solutions of disinfectant. High-touch surfaces include seats, seatbacks, tray tables, overhead bins, and other surfaces in frequent contact with passengers. These manual procedures may include time constraints, labor costs, and consistency issues. As one example, a manual wipe-down or spray-down may take longer than an allotted turnaround time during grounding, resulting in longer wait times and/or insufficient cleaning. As another example, a manual wipe-down or spray-down may have a relatively high labor cost, as additional workers may be employed to adequately clean the cabin. As another example, a manual wipe-down or spray-down may have varying consistency and material expenditure due to variations in human, machine, or material performance.

SUMMARY

In general, the disclosure describes techniques for disinfecting an aircraft cabin using an existing ventilation system of an aircraft. A non-peroxide disinfectant is injected into an environmental control system of an aircraft in an amount sufficient to disinfect surfaces of the aircraft cabin. This non-peroxide disinfectant may be aerosolized using relatively low power equipment to form droplets sufficiently small to travel through the environmental control system. A pressurized air source, such as an onboard air conditioner pack or offboard air conditioning ground cart, discharges air, including the disinfectant, into the aircraft cabin. The disinfectant deposits on various surfaces of the aircraft cabin, including surfaces that may be relatively difficult to access using wipes or sprays. Throughout the disinfecting technique, cabin air may be discharged from the cabin to maintain flow through the aircraft cabin, such as from one or more outflow valves or through filtered recirculation lines. In this way, the aircraft cabin may be disinfected relatively quickly, consistently, and/or inexpensively compared with manual or peroxide-based disinfecting procedures.

In some examples, the disclosure describes a method for disinfecting an aircraft cabin that includes injecting a non-peroxide disinfectant into an environmental control system of an aircraft and discharging cabin supply air through the environmental control system to discharge the non-peroxide disinfectant into the aircraft cabin. In some instances, the method includes aerosolizing the disinfectant into a plurality of liquid droplets while injecting the disinfectant into the environmental control system. In some instances, the injected disinfectant includes a non-corrosive, non-toxic disinfectant, such that the disinfectant may be discharged into the aircraft cabin in the presence of personnel in the aircraft cabin.

In some examples, the disclosure describes a system for disinfecting an aircraft cabin that includes a disinfectant assembly and one or more supply air sources. The disinfectant assembly is configured to inject a non-peroxide disinfectant into an environmental control system of an aircraft. The one or more supply air sources are configured to discharge supply air into the environmental control system to discharge the non-peroxide disinfectant into the aircraft cabin.

The details of one or more examples are set forth in the accompanying drawings and the description below. Other features, objects, and advantages will be apparent from the description and drawings, and from the claims.

BRIEF DESCRIPTION OF THE FIGURES

The details of one or more examples are set forth in the accompanying drawings and the description below. Other features, objects, and advantages will be apparent from the description and drawings, and from the claims.

FIG. 1A is a schematic block diagram illustrating an example system for disinfecting an aircraft cabin.

FIG. 1B is a schematic block diagram illustrating an example system for disinfecting an aircraft cabin.

FIG. 1C is a schematic block diagram illustrating an example system for disinfecting an aircraft cabin.

FIG. 2 is a flowchart of an example technique for disinfecting an aircraft cabin.

DETAILED DESCRIPTION

In general, this disclosure describes use of a ventilation system, such as an environmental control system (ECS) of an aircraft, to distribute a non-peroxide disinfectant onto surfaces of a cabin. FIG. 1A is a schematic block diagram illustrating an example system 100A for disinfecting a cabin 102 that utilizes existing infrastructure of a ventilation system to power and distribute a non-peroxide disinfectant. While system 100A will primarily be described with respect to an aircraft, it will be understood that the disclosed systems and techniques can be used for other enclosed personnel volumes that include relatively distributed, high flow ventilation systems. For example, a watercraft, spacecraft, or other air-limited, controlled environment may utilize the disclosed systems and techniques for disinfecting surfaces within the controlled environment.

Cabin 102 is configured to house personnel, such as passengers or crew members, and may include various surfaces that are frequently touched by personnel in cabin 102. For example, an aircraft cabin may include seats, tray tables, and storage compartments that are frequently touched or operated by passengers or crew members. In addition to being frequently touched, these surfaces may also form a relatively complex surface area profile.

System 100A includes an environmental control system (ECS) 104. ECS 104 is configured to distribute conditioned air into and throughout cabin 102. For example, ECS 104 may receive pressurized air, such as bleed air from an engine or compressed air from a cabin air compressor, cool the pressurized air, such as using one or more heat exchangers and/or air conditioning packs, and distribute this conditioned air throughout cabin 102. ECS 104 may be configured to supply conditioned air to cabin 102 under a variety of operating conditions, including grounded and/or docked conditions in which a cooling load is relatively high. To more evenly distribute air to personnel in cabin 102, ECS 104 may be configured to distribute air throughout cabin 102 in a relatively dispersed manner.

Figure 1A:
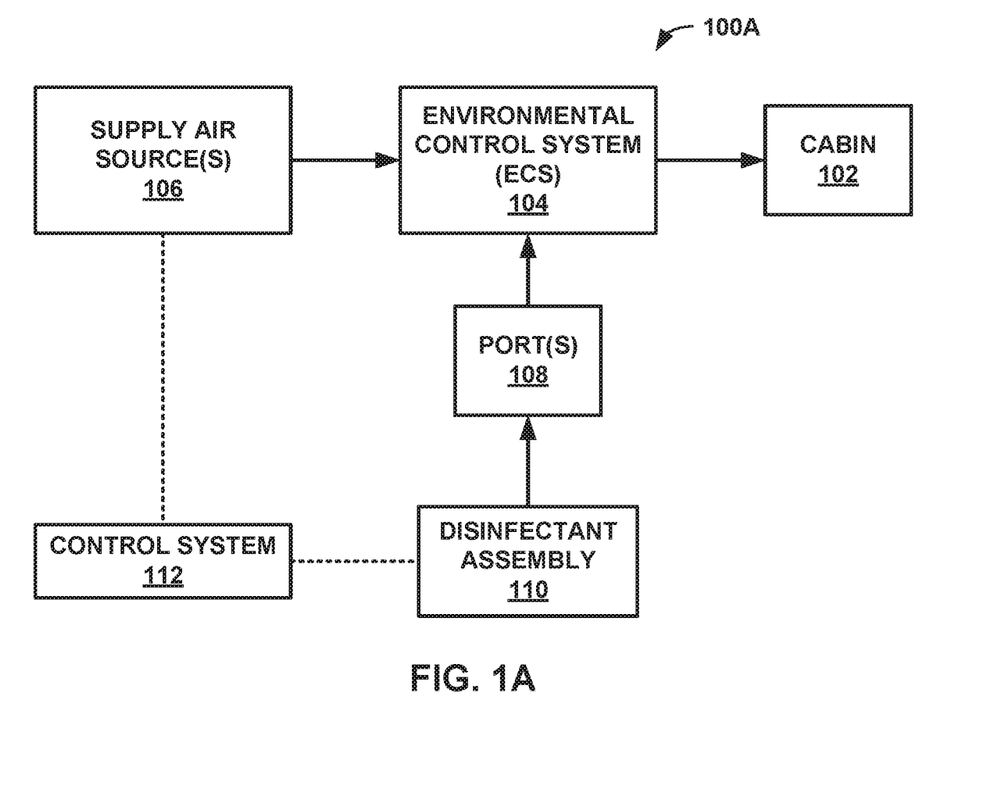

System 100A includes one or more supply air sources 106 (individually, "supply air source 106"). While shown as separate from ECS 104, in some instances, supply air source 106 may be part of ECS 104, such as will be explained in FIG. 1B below. Supply air source 106 is configured to discharge pressurized air into an air distribution system of ECS 104. System 100 also includes one or more ports 108 configured to provide fluidic access to ECS 104. For example, when an aircraft is at a grounded condition, ports 108 may provide access to supplemental conditioned air for supplying conditioned air to cabin 102.

The personnel housed in cabin 102 may be vulnerable to microorganisms, such as bacteria and viruses. These microorganisms may be deposited onto surfaces of cabin 102 by previous personnel in cabin 102, such as previous passengers or flight crew members, and may survive on surfaces for relatively long periods of time that surpass a turnover time between flights.

According to principles described herein, system 100A is configured to disinfect surfaces of cabin 102 by using ECS 104 to distribute a non-peroxide disinfectant into cabin 102. System 100A includes disinfectant assembly 110. Disinfectant assembly 110 is configured to connect to one or more ports 108 and inject a non-peroxide disinfectant into ECS 104. The non-peroxide disinfectant may be configured to kill microorganisms on surfaces in cabin 102 while remaining relatively benign to personnel in cabin 104 or materials in ECS 104. Supply air source 106 may be configured to discharge pressurized air into ECS 104 to discharge the non-peroxide disinfectant into cabin 102. For example, the non-peroxide disinfectant may deposit onto most high-touch surfaces of cabin 102 and kill most bacteria and/or denature most viruses on the high-touch surfaces.

System 100A includes control system 112. Control system 112 may be configured to control one or more components of system 100A to disperse the disinfectant throughout cabin 102. For example, control system 112 may be configured to control supply air sources 106 to discharge supply air into ECS 104 at a flow rate sufficient to achieve a desired coverage and/or residence time of the disinfectant. As another example, control system 112 may be configured to control disinfectant assembly 110 to inject disinfectant into ECS 104 at a flow rate, vapor fraction, and/or droplet size sufficient to achieve a desired final coverage and/or suspension of the disinfectant as it travels to the cabin.

By using ECS 104 to distribute the non-peroxide disinfectant through cabin 102, system 100A may quickly, thoroughly, and/or inexpensively disinfect cabin 102. Supply air sources 106 may provide a high throughput motive force for distributing the disinfectant through cabin 102, such that cabin 102 may be disinfected in a relatively short amount of time. ECS 104 may provide a relatively dispersed network of ducting and venting for distributing and drawing out the disinfectant as a vapor or aerosol throughout cabin 102.

In some examples, disinfectant assembly 110 may be configured to aerosolize the disinfectant into a plurality of liquid droplets while injecting the disinfectant into ECS 104. For example, the plurality of liquid droplets may have an average diameter between 1 and 100 micrometers, such that the droplets may remain suspended and/or entrained in the supply air during flow in the ECS 104 and fall to the surface when discharged into cabin 102, so that the droplets settle on surfaces of cabin 102. However, aerosolizing the disinfectant may use less energy than, for example, vaporizing the disinfectant. As such, aerosolizing the disinfectant while injecting the disinfectant into ECS 104 may use less power from the auxiliary power unit (APU) or other power source and permit a greater variety of disinfectants to be used.

In some examples, system 100A may be configured to disinfectant cabin 102 in the presence of personnel in cabin 102. For example, the injected disinfectant may be a non-corrosive, non-toxic disinfectant that may not be harmful in airborne concentrations required for killing microorganisms on the surface. As a result, the disinfectant may be discharged into cabin 102 in the presence of personnel in cabin 102, which may further reduce an expense of disinfecting cabin 102.

Figure 1B:
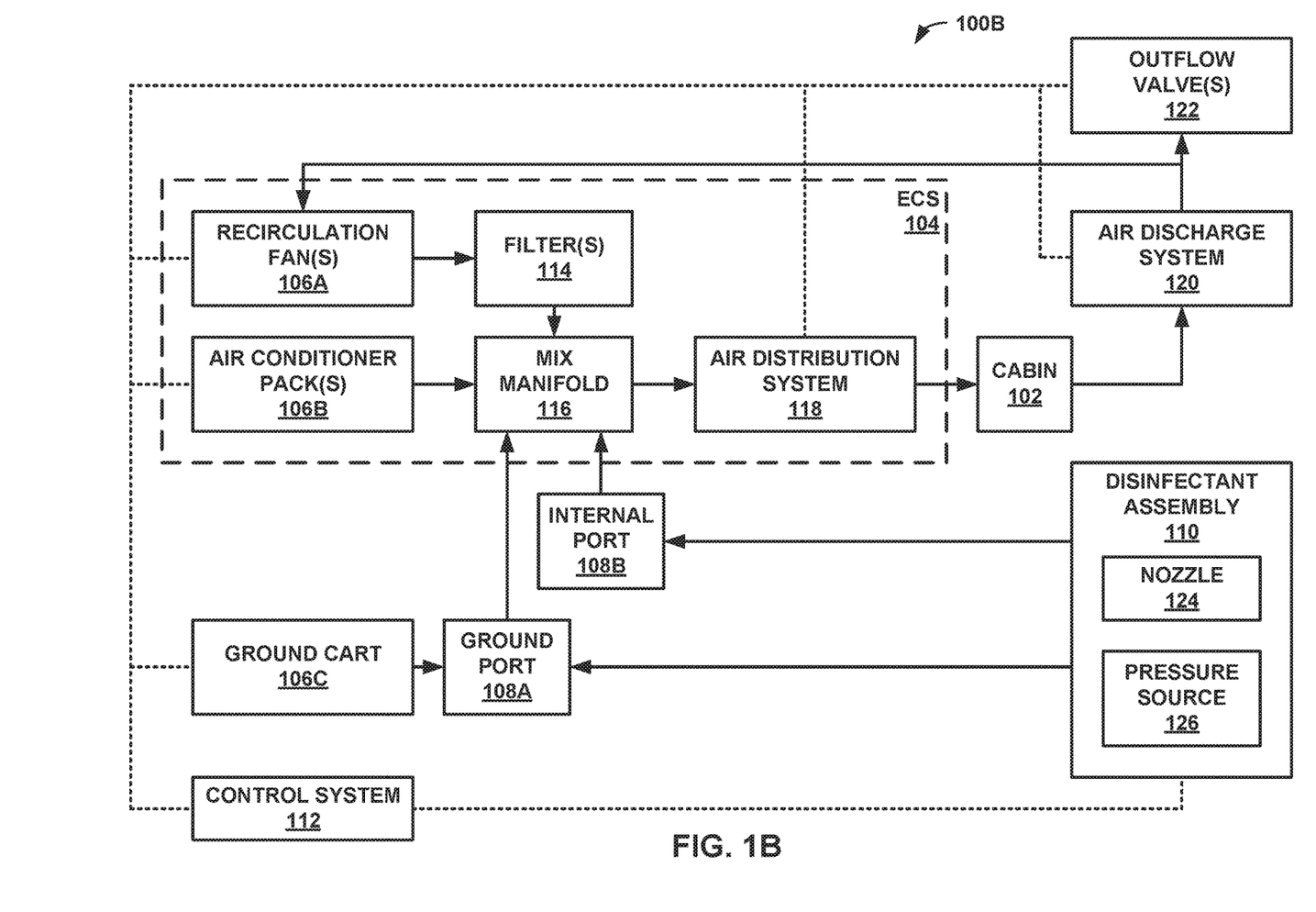

The methods described herein may be particularly suitable for disinfecting an aircraft cabin. For example, an aircraft cabin may include relatively short turnover time, operate at relatively small profit margins, and be subject to limited space at airports, such that airlines may be especially sensitive to time or cost constraints and external equipment sizing and portability. FIG. 1B is a schematic block diagram illustrating an example system 100B for disinfecting aircraft cabin 102. Cabin 102 may be disinfected using a variety of systems of an aircraft and/or available to an aircraft.

ECS 104 includes an air distribution system 118. Air distribution system 118 may be configured to distribute supply air into cabin 102. Air distribution system 118 may include a variety of components for transporting and dispersing air into cabin 102 including, but not limited to, ducting, air vents, gaspers, and the like. Air distribution system 118 may include dispersion components, such as vents and gaspers, that are relatively well distributed throughout cabin 102. For example, air vents may be positioned regularly along an aisle of cabin 102 near a ceiling of cabin 102 and gaspers may be positioned near each seat in cabin 102.

ECS 104 may include a mix manifold 116. Mix manifold 116 may be configured to receive air from a variety of sources and discharge the mixed air into air distribution system 118. To receive air from outside ECS 104, mix manifold 116 includes one or more ports configured to provide fluidic access to ECS 104, including ground port 108A and internal port 108B. Ground port 108A may be accessible from outside an aircraft and configured to receive air while an aircraft is grounded. For example, ground port 108A may be configured to couple to one or more pieces of machinery, such as ground cart 106C, configured to supply one or more pressurized fluids, such as air, to mix manifold 116. Internal port 108B may be accessible from inside an aircraft and configured to receive air while an aircraft is grounded or in flight. For example, internal port 108B may be configured to couple to one or more pieces of machinery configured to supply one or more pressurized fluids to mix manifold 116. While shown as connected to mix manifold 116, in some examples, one or more internal ports 108B may be connected at other locations within ECS 104.

Mix manifold 116 may be configured to receive air from supply air sources from within ECS 104, including recirculation fans 106A and air conditioner packs 106B, and/or air from supply air sources outside ECS 104, including ground cart 106C (collectively referred to as "supply air sources 106"). Supply air sources 106 may be configured, alone or in combination, to discharge supply air into mix manifold 116 to distribute disinfectant received by ports 108 into air distribution system 118

Air conditioner packs 106B may be configured to receive pressurized air, such as bleed air from the engines or compressed air from one or more cabin air compressors powered by an auxiliary power unit, and cool the pressurized air to supply conditioned air for use in cabin 102. For example, when an aircraft is grounded, an auxiliary power unit may power air conditioner packs 106B to cool pressurized air to produce conditioned air for cabin 102. Air conditioner packs 106B may be configured to supply air to cabin 102 at a wide range of temperatures.

Recirculation fans 106A may be configured to draw pressurized cabin air from cabin 102 into mix manifold 116 to mix with supply air from air conditioner packs 106B and/or ground cart 106C. One or more filters 114 may be positioned upstream or downstream of recirculation fans 106A, such that recirculation fans 106A may be configured to draw air through one or more filters 114 to clean the cabin air for further use in cabin 102. In some instances, filters 114 may be configured to remove disinfectant from recirculated air.

Ground cart 106C may be configured to connect to ECS 104 via a ground port 108A and discharge conditioned air from an external air conditioning system through ground port 108A. For example, when an aircraft is grounded, rather than use fuel to power ECS 104 to supply conditioned air to cabin 102, ECS 104 may receive conditioned air from ground cart 106C. Ground cart 106C may be configured to supply air to cabin 102 at a wide range of temperatures and flow rates. For example, while air conditioner pack 106B may be relatively limited in size due to weight concerns, ground cart 106C may be configured to supply a relatively wide range of flow rates.

System 100B includes an air discharge system 120. Air discharge system 120 may be configured to discharge cabin air from cabin 102. Air discharge system 120 may include a variety of components for drawing and transporting air from cabin 102 including, but not limited to, ducting, air vents, and the like. Air discharge system 120 may include dispersion components, such as vents, that are relatively well distributed throughout cabin 102. For example, air vents may be positioned regularly along a fuselage of cabin 102 near a floor of cabin 102.

Air discharge system 120 may be configured to recirculate air to recirculation fans 106A or discharge air from the aircraft through one or more outflow valves 122. Outflow valves 122 may be configured to discharge cabin air from air discharge system 120, such as in a particular position, at a particular flow rate, or to maintain cabin 102 at a particular pressure.

Disinfectant assembly 110 may be configured to inject disinfectant into mix manifold 116 through ground port 108A and/or internal port 108B. For example, disinfectant assembly 110 may be configured to couple to at least one of ground port 108A and/or internal port 108B. In some examples, disinfectant assembly 110 may include one or more pressure sources 126 configured to discharge the disinfectant into mix manifold 116 through ground port 108A and/or internal port 108B. For example, ECS 104 may be at a positive pressure, such that pressure source 126 may be configured to create a pressure differential to inject the disinfectant at a desired flow rate. Disinfectant assembly 110 may include one or more nozzles 124. Nozzle 124 may be configured to discharge disinfectant having various of injection characteristics including, but not limited to, flow rate, droplet size (e.g., diameter), and the like. A variety of nozzles may be used including, but not limited to, spray nozzles, impingement nozzles, whirl nozzles, misting nozzles, internal mix/air atomizing nozzles, external mix/air atomizing nozzles, nebulizing nozzles, and the like. For example, nozzle 124 may be capable of achieving droplet sizes between about 100 nanometers and about 100 micrometers.

While disinfectant assembly 110 is illustrated in FIG. 1B as being external to ECS 104, in some examples, disinfectant assembly 110 may be part of ECS 104. For example, attaching an external disinfectant assembly 110 through ground port 108A may be relatively time-consuming and/or may tie up a high pressure or low pressure ground port that may be used for another purpose, such as supplying conditioned air to ECS 104. As such, disinfectant assembly 110 may be present onboard the aircraft and configured to inject the disinfectant without assembly of additional equipment. For example, while not shown in FIG. 1B, disinfectant assembly 110 may include a tank configured to store a volume of disinfectant for performing one or more disinfectant procedures described herein. In this way, disinfectant assembly 110 may disinfect cabin 102 in less time than a disinfectant assembly that may be attached through one or more ground ports 108A.

In some instances, disinfectant assembly 110 may be configured to inject the disinfectant as a vapor. For example, a vapor may be less likely to deposit through condensation on surfaces between disinfectant assembly 110 and cabin 102, such as ducting of air distribution system 118, compared to aerosols. In some examples, disinfectant assembly 110 may include low temperature vaporization equipment configured to vaporize the disinfectant at relatively low temperatures to form a vapor.

In some instances, disinfectant assembly 110 may be configured to inject the disinfectant as an aerosol. An aerosol may include a liquid droplet that is sufficiently small to become entrained and/or suspended in air for a desired distance or amount of time. For example, vaporizing the disinfectant may be relatively energy intensive, and may require relatively large equipment. In contrast, aerosolizing (e.g., fogging, nebulizing, spraying, etc.) the disinfectant into liquid droplets may require less energy to produce a plurality of liquid droplets that are sufficiently small to travel through ECS 104 and remain suspended in cabin 102 to impact surfaces.

Disinfectant assembly 110 is configured to inject a non-peroxide disinfectant. For example, hydrogen peroxide may disinfect surfaces and breakdown into benign components (water vapor and oxygen). However, prior to breaking down, hydrogen peroxide may react with and corrode various materials, including materials used in ECS 104 such as rubber or polymers for seals and gaskets. For example, hydrogen peroxide may degrade epoxy, LDPE, natural rubber, nylon, and other polymers at relatively low hydrogen peroxide concentrations (e.g., less than about 10%). Further, hydrogen peroxide vapor may be toxic when ingested, inhaled, or in contact with skin or eyes, and has an odor that requires long aeration times before people can return. As a result, hydrogen peroxide may not be used with personnel in cabin 102.

A variety of non-peroxide disinfectants may be injected by disinfectant assembly 110. In some examples, the disinfectant may be relatively non-reactive with materials in environmental control system 104 and cabin 102, such as ducting and gaskets of ECS 104; carpets, seats, seatbelts, windows, screens, and performance metal alloys of cabin 102, and vents of air distribution system 118 and air discharge system 120. Relatively non-reactive disinfectants that may be used include, but are not limited to, stabilized chlorine dioxide, and the like. In some examples, the disinfectant may be biologically safe after depositing on surfaces of cabin 102. For example, the disinfectant, once deposited, may be biologically safe when contacting skin or ingested into the body, or when inhaled at trace concentrations in the air. In some examples, the disinfectant may be biologically safe in the air at concentrations used to disinfect surfaces. For example, the disinfectant may be biologically safe when inhaled. Biologically safe disinfectants that may be used include, but are not limited to, stabilized chlorine dioxide, and the like. In some examples, the disinfectant may be relatively easily aerosolized. For example, the disinfectant may be selected for various properties, such as viscosity, surface tension, specific gravity, and other properties related to an ability to form aerosol droplets in the air and resist agglomeration.

Control system 112 may be communicatively coupled to and configured to control various components of system 100B including, but not limited to, recirculation fans 106A, air conditioner packs 106B, ground cart 106C, disinfectant assembly 110, air distribution system 118, air discharge system 120, and/or outflow valves 122. Control system 112 may include or may be one or more processors or processing circuitry, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some examples, the functionality of computing device 40 may be provided within dedicated hardware and/or software modules.

While not shown, control system 112 may include one or more sensors distributed through system 100B that may include, but are not limited to, aerodynamic particle sensors, concentration sensors, humidity sensors, temperature sensors, flow rate sensors, valve position sensors, and any other sensors that may provide a measurement indication of an operating parameter of system 100B. For example, system 100B may include one or more concentration sensors configured to detect a concentration of disinfectant in cabin 102, one or more humidity sensors configured to detect a humidity, and therefore indicate a concentration of disinfectant, in cabin 102, one or more temperatures sensors configured to detect a temperature of ECS 104 or cabin 102, one or more valve position sensors configured to detect a valve position of outflow valves 122, one or more speed sensors configured to detect a speed of recirculation fans 106A, one or more flow rate sensors configured to detect a flow rate of recirculation fans 106A, air conditioner packs 106B, and/or ground cart 106C, one or more flow rate sensors configured to detect a flow rate of disinfectant from disinfectant assembly 110, one or more nozzle position sensors configured to detect a position of nozzle 124, one or more aerodynamic particle sensors to detect a droplet size of the disinfectant, and the like. Another is simply the weight of the disinfectant to track the amount injected.

Control system 112 may be configured to control parameters of system 100B such that the disinfectant is discharged onto surfaces of cabin 102 in a sufficient amount, and optionally within a sufficient time, to kill most microorganisms of interest on high-touch surfaces. Control system 112 may be configured to control a variety of parameters of system 100B including, but not limited to, a droplet size of an aerosolized disinfectant (e.g., by controlling nozzle 124), a flow rate of disinfectant into mix manifold 116 (e.g., by controlling pressure source 126), a flow rate of supply air into mix manifold 116 (e.g., by controlling recirculation fans 106A, air conditioner packs 106B, and/or ground cart 106C), a temperature of supply air into mix manifold 116 (e.g., by controlling recirculation fans 106A, air conditioner packs 106B, and/or ground cart 106C), a distribution location of supply air into cabin 102 (e.g., by controlling air distribution system 118), a discharge location of cabin air from cabin 102 (e.g., by controlling air discharge system 120), a flow rate of cabin air from cabin 102 to an external environment (e.g., by controlling outflow valves 122), and/or a recirculation flow rate of cabin air from cabin 102 to mix manifold 116 (e.g., by controlling recirculation fans 106A).

Control system 112 may be configured to control components of disinfectant assembly 110, such as nozzle 124 and/or pressure source 126, to aerosolize the disinfectant and produce aerosolized liquid droplets having an average droplet size or range of droplet sizes. The aerosolized liquid droplets may be sufficiently small that the liquid droplets are carried through ECS 104 into cabin 102 without substantially settling or impinging on surfaces of ECS 104. For example, an amount of time for a liquid droplet to settle in air may be related to a size of the liquid droplet and a flow rate of the liquid droplet, such that liquid droplets having smaller diameters may remain suspended or entrained in air for a longer period of time before settling on a surface. In some examples, an average droplet size of the aerosolized liquid droplets may be less than about 100 micrometers, such as less than about 10 micrometers. However, an amount of energy to produce a liquid droplet of a particular diameter may also be related to a size of the liquid droplet, such that liquid droplets having smaller diameters may require a greater amount of energy to produce. As such, when operating nozzle 124, control system 112 may be configured to control nozzle 124 to produce liquid droplets that are sufficiently small remain in the air and produce a desired coverage, while also limiting an amount of energy used to aerosolize the liquid droplets. In some examples, an average droplet size of the aerosolized liquid droplets may be between about 100 nanometers and about 100 micrometers. To control the droplet size, control system 112 may control a pressure of pressure source 126, a pressure of a disinfectant source, a shape or orientation of nozzle 124, and the like. For example, control system 112 may receive a droplet size setpoint for nozzle 124 and send a control signal to disinfectant assembly 110 configured to produce a droplet size that satisfies the droplet size setpoint.

In some examples, control system 112 may be configured to control nozzle 124 to produce aerosolized liquid droplets that may vaporize between nozzle 124 and cabin 102. For example, rather than use energy to vaporize the disinfectant, disinfectant assembly 110 may utilize energy absorbed from supply air from supply air sources 106 or pressurized air from pressure source 126 to vaporize the aerosolized liquid droplets as the liquid droplets travel through ECS 104. For example, control system 112 may receive a vapor fraction setpoint for cabin 102 and send a control signal to disinfectant assembly 110 configured to produce a droplet size that satisfies the vapor fraction setpoint. In this way, a relatively low amount of energy may be used to produce a vapor disinfectant.

Control system 112 may be configured to control the flow rate of air and disinfectant into mix manifold 116 based on a desired coverage of disinfectant in cabin 102. For example, deposition of disinfectant of surfaces of cabin 102 may be caused by condensation of vapor disinfectants and settling and impaction of aerosolized disinfectants. The rate of deposition may be related to a concentration of the disinfectant in cabin 102 such that, at higher concentrations, the disinfectant may deposit at higher rates. A concentration of the disinfectant may be dependent on a variety of operating parameters of system 110B including, but not limited to, a flow rate of supply air into mix manifold 116, a flow rate of cabin air from cabin 102, a flow rate of disinfectant into mix manifold, and a percentage of disinfectant that reaches cabin 102. As such, control system 112 may be configured to control a speed of recirculation fans 106A, a flow rate of supply air from air conditioner packs 106B, a flow rate of supply air from ground cart 106C, a flow rate of cabin air from outflow valves 122, and a flow rate of disinfectant from disinfectant assembly 110 to achieve a desired coverage of disinfectant in cabin 102. For example, control system 112 may receive a concentration setpoint corresponding to a desired coverage and send one or more control signals to supply air sources 106, outflow valves 122, and/or disinfectant assembly 110 to maintain a coverage (e.g., a concentration of disinfectant in cabin 102 within the concentration setpoint and/or according to a programmed concentration profile) for a duration to achieve the desired coverage. In some instances, control system 112 may operate system 100B based on any combination of fixed flow rates and variable flow rates of supply air and disinfectant, such as fixed flow rates of supply air and variable flow rates of disinfectant, variable flow rates of supply air and fixed flow rates of disinfectant, fixed flow rates of supply air and the disinfectant, and variable flow rates of supply air and the disinfectant.

In some examples, control system 112 may be configured to control a flow rate of air into mix manifold 116 and, correspondingly, air distribution system 118 to achieve a desired flow rate of supply air into cabin 102. In addition to concentration of the disinfectant in the air of cabin 102, a rate of deposition of the disinfectant may be related to the flow rate of the air carrying the disinfectant through cabin 102 and an amount of turbulence in cabin 102. For example, the flow rate will affect a pattern of swirl, and thus mixing, in cabin 102. Higher flow rates may increase mixing and thus promote contact of suspended particles with surfaces. For example, a relatively high flow rate may flow a greater amount of disinfectant through cabin 102 in a particular period of time at a particular flow rate. However, a flow rate that is too high may create too much turbulence, such that small liquid droplets may not deposit onto surfaces of cabin 102, while a flow rate that is too low may not create enough turbulence, such that larger liquid droplets may not mix and distribute to surfaces of cabin 102. The flow rate may also determine residence time of disinfectant in cabin 102 (i.e. slower rates lead to longer residence times of disinfectant in cabin 102). As such, control system 112 may be configured to control the flow rate to sufficiently distribute the disinfectant through cabin 102 while depositing the disinfectant within any predetermined time constraints. For example, control system 112 may be configured to receive a flow rate setpoint or duration setpoint and send one or more control signals to supply air sources 106 and outflow valves 122 to operate at the flow rate setpoint or for the duration setpoint.

Control system 112 may be configured to control a flow rate of disinfectant into mix manifold 116. For example, control system 112 may be configured to receive a flow rate setpoint of the disinfectant from disinfectant assembly 110 or concentration/coverage setpoint for the disinfectant in cabin 102 and send one or more control signals to nozzle 124 and/or pressure source 126 to control an air pressure, liquid pressure, and/or nozzle configuration to produce a flow rate of the disinfectant that achieves the flow rate setpoint or concentration/coverage setpoint. In some examples, control system 112 may be configured to inject a particular amount of disinfectant or inject disinfectant for a particular amount of time. For example, control system 112 may be configured to receive a disinfectant quantity or duration setpoint and send one or more control signals to control nozzle 124 and/or pressure source 126 to control disinfectant assembly to discharge the disinfectant up to the quantity or duration setpoint.

In some examples, control system 112 may be configured to control a temperature of supply air to cabin 102. For example, higher temperatures may promote vaporization and smaller aerosolized droplet sizes. On the other hand, colder temperatures may promote maintaining fogging. As such, control system 112 may control the temperature of supply air to cabin 112 according to a desired vapor fraction, droplet size, and/or residence time of the disinfectant.

In some examples, control system 112 may be configured to control a speed of recirculation fans 106A to preserve disinfectant for use in cabin 102. For example, as mentioned above, supply air may be discharged into cabin 102, and correspondingly cabin air may be removed from cabin 102, at flow rates to create various flow conditions within cabin 102 that may aid in deposition of the disinfectant on various surfaces within cabin 102. However, rather than discharging cabin air, which may include disinfectant, through outflow valves 122, at least a portion of the cabin air may be recirculated back into mix manifold 116. For example, vapor disinfectant may pass through filters 114 without being removed from the recirculated air. In this way, disinfectant may be recirculated through cabin 102.

In some examples, control system 112 may be configured to control a speed of recirculation fans 106A to remove disinfectant from cabin 102. For example, once the disinfectant has been deposited on various surfaces in cabin 102 at the end of the treatment procedure, the excess disinfectant remaining in the cabin air may be removed from cabin 102 to prepare for the next flight. However, during grounded conditions, discharge of the disinfectant may be hazardous to personnel near outflow valves 122 or may violate various regulations regarding environmental discharge. Rather than discharging the cabin air through outflow valves 122 to the environment, at least a portion of the cabin air may be recirculated through filters 114 to remove disinfectant from the cabin air. For example, filters 114 may be configured to remove vapor and/or liquid droplets of disinfectant from the cabin air, such as by using conventional air filters for cabin 102 or special use filters 114. In this way, disinfectant may be removed from cabin 102 without discharge overboard.

In some examples, control system 112 may be configured to control a spatial distribution of the disinfectant through cabin 102. For example, air distribution system 118 and/or air discharge system 120 may include various valves or other flow restriction devices that may control a flow of the supply air into or from cabin 102, respectively. Various flow conditions in air distribution system 118, air discharge system 120, and/or cabin 102 may create a concentration of the disinfectant in cabin 102 that may not be uniform. As such, control system 112 may be configured to control air distribution system 118 and/or air discharge system 120 to create various concentration profiles through cabin 102. For example, control system 112 may be configured to receive concentration measurements from one or more regions of cabin 102 (e.g., fore, mid, and aft) and send one or more control signals to air distribution system 118 and/or air discharge system 120 to maintain the one or more regions at a concentration setpoint.

Figure 1C:
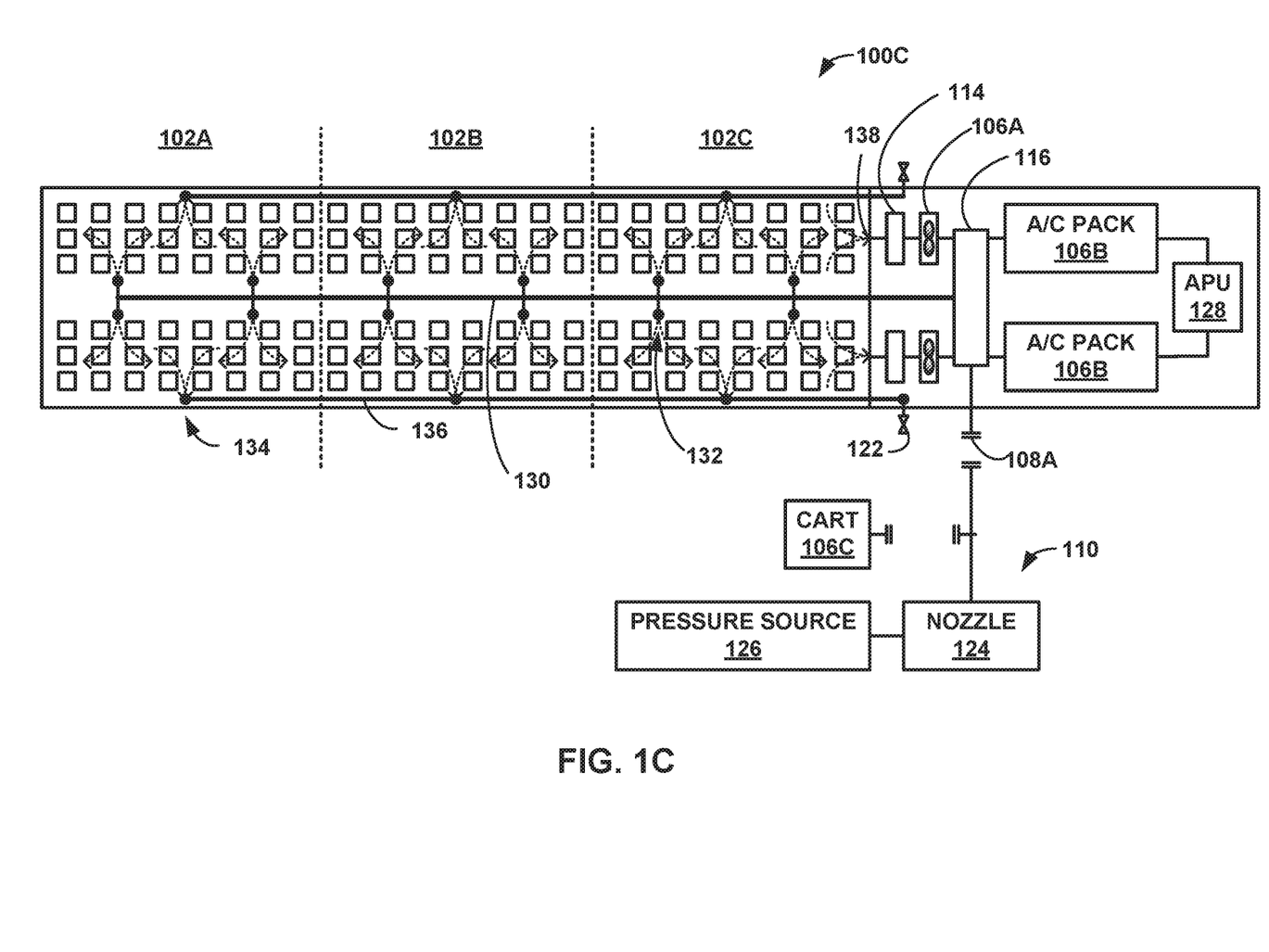

FIG. 1C is a schematic top view diagram illustrating an example system for disinfecting an aircraft cabin. Operation of system 100C will be described with reference to FIG. 2, which is a flowchart of an example technique for disinfecting an aircraft cabin. However, system 100C may be used with other techniques, and the method of FIG. 2 may be performed by other systems.

Referring to FIG. 1C, system 100C may include a fore zone 102A, a mid zone 102B, and an aft zone 102C of cabin 102. An air distribution system of system 100C may include distribution ducting 130 along a center aisle and one or more distribution vents 132. Ducting 130 and vents 132 are configured to transport and distribute the disinfectant from mix manifold 116 to the various zones 102A, 102B, and 102C of the cabin. An air discharge system of system 100C may include discharge ducting 136 along a side fuselage and one or more discharge vents 134. Ducting 136 and vents 134 are configured to remove and transport the disinfectant from the various zones 102A, 102B, and 102C to outflow valves 122.

Figure 2:
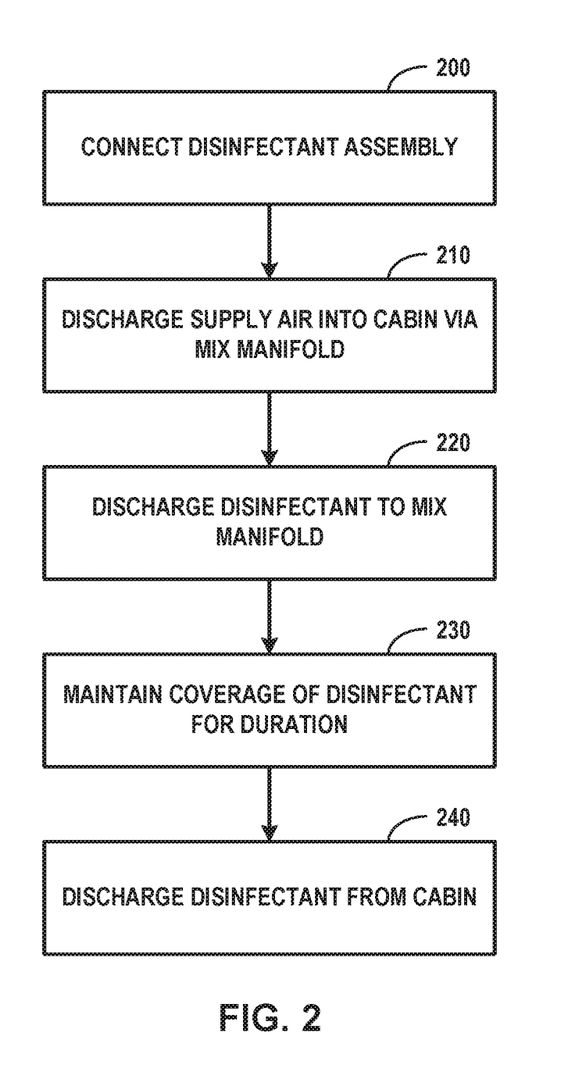

Referring to FIG. 2, the method of FIG. 2 includes connecting disinfectant assembly 110 to one or more ports 108 (200). In the example of FIG. 1C, disinfectant assembly 110 is connected to ground port 108A.

The method of FIG. 2 includes discharging supply air into cabin 102 via mix manifold 116 (210). For example, control system 112 may control APU 128 to supply compressed air to each air conditioner pack 106B ("A/C Pack 106B") to discharge clean supply air into mix manifold 116 and/or control recirculation fans 106A to discharge cabin air into mix manifold 116. In some examples, ground cart 106C ("Cart 106C") may be connected to mix manifold 116 through ground port 108A, such that control system 112 may control ground cart 106C to discharge supply air into mix manifold 116.

The method of FIG. 2 includes injecting a non-peroxide disinfectant into mix manifold 116 (220), such that the non-peroxide disinfectant is discharged into cabin 102. For example, control system 112 may control nozzle 124 and/or pressure source 126 to discharge the disinfectant into mix manifold 116. In some examples, control system 112 may control nozzle 124 and/or pressure source 126 to discharge the disinfectant to maintain a constant application in cabin 102 or for a particular amount of time in order to achieve the desired coverage.

In some examples, the method of FIG. 2 may include aerosolizing the disinfectant into a plurality of liquid droplets while injecting the disinfectant into mix manifold 116. The plurality of liquid droplets may have an average diameter between about 100 nanometers and about 100 micrometers, such as between about 5 micrometers and about 30 micrometers. In some examples, the injected disinfectant comprises a non-corrosive, non-toxic disinfectant, such that the disinfectant is discharged into the aircraft cabin in the presence of personnel in the aircraft cabin.

The method of FIG. 2 may include maintaining a coverage of the disinfectant in cabin 102 for a duration of time (230). For example, to kill microorganisms on various surfaces of cabin 102, a particular amount of the disinfectant may be maintained for a period of time sufficient for the disinfectant to deposit with a sufficient coverage (i.e., disinfectant per surface area) on the surfaces and kill the microorganisms, such as greater than 95%, preferably greater than 99%, and more preferably greater than 99.9%.

A particular kill ratio is related to an amount of disinfectant per surface area. For a relatively uniformly spread disinfectant, an amount of disinfectant injected per surface area may be correlated to the kill ratio (which may assume that surfaces are evenly contaminated), and may vary based on a type of disinfectant. In some examples, control system 112 may reduce a flow rate of supply air into mix manifold 116 to reduce flow of the disinfectant through cabin 102 and allow time for the disinfectant to deposit. For example, aerosolized liquid droplets may deposit by settling on the surfaces, which may be a function of residence time in cabin 102.

In some examples, the method of FIG. 2 includes recirculating cabin air. For example, to maintain an amount of the disinfectant in cabin 102 for a particular period of time to achieve sufficient coverage, control system 112 may control a speed of recirculation fans 106A to recirculate cabin air that may include the disinfectant. In this way, an amount of the disinfectant may be preserved within cabin 102 and ECS 104.

The method of FIG. 2 includes discharging cabin air from cabin 102 (240). For example, after maintaining the coverage of the disinfectant in cabin 102 for a particular duration sufficient to deposit the disinfectant on surfaces in cabin 102, control system 112 may discharge the disinfectant from cabin 102. Control system 112 may control a flow rate of cabin air discharged through outflow valves 122. Control system 112 may also control a flow rate of supply air from the various supply air sources 106 into cabin 102, such that cabin 102 may be flushed relatively quickly. In some examples, control system 112 may control a speed of recirculation fans 106A such that filters 114 may remove the disinfectant from the cabin air.

Experimental Methods

An ability of an environmental control system (ECS) to introduce an aerosol disinfectant to an aircraft cabin and achieve the required coverage, and an efficacy of the disinfectant when it arrives in the cabin, may be tested as described below. Both a disinfectant and water, as a surrogate for the disinfectant, may be used for the test. Various variables may be considered including, but not limited to, aerosol particle size, aerosol flow rate, air conditioner pack temperature, air conditioner pack flow rate, observation of the disinfectant amount based on position in the cabin, an outlet flow valve position, and a recirculation fan setting. The disinfectant may be injected into a mix manifold or other area of the ECS, and may be transported by various methods, such as by the air conditioner pack, recirculation fans, or ground cart air.

The test involves using a piece of equipment (e.g., a nozzle) to produce an aerosol. The nozzle may inject the compound aerosol into an 8-inch low pressure ground port connection (typically used to hook up the ground cart hose), that is located underneath the aircraft. The nozzle may inject the compound into the mix manifold, if accessible. The nozzle may inject the compound into the ducting leading to the mix manifold. The compound may be run at a flow rate between about 5-20 L/hr. The aircraft cabin may be outfitted with humidity sensors and aerosol sensors and loggers in various locations to obtain a description of the location of the compound. Based on these values, an amount of injected compound that did not reach the aircraft cabin or was not maintained in the aircraft cabin may be determined. Petri plates with filter paper contaminated with *Serratia marcescens* Bizio (ATCC 14756) may be dispersed around the cabin for bacteria enumeration studies to test the efficacy of the compound entering the cabin.

Equipment used to operate the test may include a nozzle configured to produce an aerosol of the compound; a port plate configured to fit the ground port and permit feed-through for a nozzle line; a compressor configured to produce pressurized air at a flow rate sufficient to inject the compound into the ECS; and a charger configured to produce a liquid pressure sufficient to discharge the compound at a desired flow rate. Equipment used to measure parameters of the test may include one or more aerodynamic particle sizers configured to measure various sizes of droplets/particles of aerosol compound, located in a center aisle of the aircraft cabin; one or more temperature/humidity meters configured to measure a temperature and/or humidity of the aircraft cabin distributed throughout the aircraft cabin; one or more gelatin slides configured to capture aerosol compounds, distributed through the aircraft cabin; and one or more petri dishes configured host bacteria, distributed throughout the aircraft cabin.

Prior to running the test, several preparation steps may be performed, such as confirming that the spraying equipment (e.g., nozzles, compressor, and charger) may be producing expected aerosol, such as an expected liquid droplet size; taking outside temperature and humidity readings; taking a baseline reading of all instrumentation on board (e.g., air conditioner pack running); making note of cabin layout (where have bins been removed, where is distribution non-standard, etc.); and filling and pressurizing the charger with DI water or disinfectant.

Running the test may involve connecting the ground port adapter to the air conditioning ground port (low pressure port), ensuring a spray wand extends past ground port check valves, if applicable, holds flappers open, if applicable, and ensuring that the port adapter is properly seated. The APU may be started to operate the air conditioner packs to provide a cool air stream. However, alternative test set ups may include use of a ground cart without the APU, or an HP ground cart to run the APU. The isolation valve may be selected to OFF and a single air conditioner pack selected to AUTO or Normal, thereby setting the air conditioner pack to Single Pack High flow schedule, which may lower than the APU High flow schedule. This schedule may be, for example, approximately 90 lb/min on a Boeing 737. The recirculation fan switches may be set to OFF; however, if warmer air flows are desirable, the recirculation fans may be set to ON without the APU operating the air conditioner pack or packs. The cockpit and cabin temperature selectors may be set to COLD, such that an air conditioner pack outlet temperature may remain above freezing and an air conditioner pack temperature modulated to achieve a temperature of approximately 60° F. in each zone.

Compound flow may be initiated from the sprayer equipment. Once the compound is fully discharged, the sprayer equipment may be turned off. In some instances, to aid in settling of the compound, the air conditioner pack may be turned off for a period of time, such as about 10 minutes.

The cockpit and cabin temperature selectors may be returned to NORM and the recirculation fan switches may be returned to AUTO/ON. The isolation valve may be selected to AUTO and the air conditioner packs may be selected to HIGH to ventilate the cabin at a maximum rate and allow cabin to ventilate for 5 minutes before resuming normal operation.

After the test, the sprayer equipment may be shut off and the air conditioner pack or recirculation fans run to clear the aircraft cabin of the compound and return the concentration of the compound to a baseline for a next test.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Select examples of the present disclosure include, but are not limited to, the following examples.

A first example includes a method of disinfecting an aircraft cabin that includes injecting a non-peroxide disinfectant into an environmental control system of an aircraft and discharging supply air through the environmental control system to discharge the non-peroxide disinfectant into the aircraft cabin.

A second example includes the method of the first example, further including aerosolizing the disinfectant into a plurality of liquid droplets while injecting the disinfectant into the environmental control system.

A third example includes the method of the second example, wherein the plurality of liquid droplets has an average diameter less than about 10 micrometers.

A fourth example includes the method of the second or third example, wherein at least 50% of the aerosolized disinfectant vaporizes prior to entering the cabin.

A fifth example includes the method of any one of the first through fourth examples, including vaporizing the disinfectant while injecting the disinfectant into the environmental control system.

A sixth examples includes the method of any one of the first through fifth examples, wherein the disinfectant comprises a non-corrosive, non-toxic disinfectant, and wherein the disinfectant is discharged into the aircraft cabin in a presence of personnel in the aircraft cabin.

A seventh example includes the method of any one of the first through sixth examples, including discharging the disinfectant from the aircraft cabin using at least one of an outflow valve or a recirculation fan.

An eighth example includes the method of any one of the first through seventh examples, wherein the supply air is discharged through the environmental control system by at least one of an air conditioner pack or a recirculation fan of the environmental control system.

A ninth example includes the method of any one of the first through eighth examples, wherein the environmental control system includes a mix manifold, and wherein the non-peroxide disinfectant is injected into the mix manifold through a ground port.

A tenth example includes the method of any one of the first through ninth examples, including recirculating air through one or more filters to remove the disinfectant from cabin air from the cabin.

An eleventh example includes the method of any one of the first through tenth examples, including maintaining a constant application of the disinfectant to achieve the required coverage within a setpoint for a duration.

A twelfth examples includes a system for disinfecting an aircraft cabin, including a disinfectant assembly configured to inject a non-peroxide disinfectant into an environmental control system of an aircraft and one or more supply air sources configured to discharge supply air into the environmental control system to discharge the non-peroxide disinfectant into the aircraft cabin.

A thirteenth example includes the system of the twelfth example, wherein the disinfectant assembly comprises one or more nozzles configured to aerosolize the disinfectant into a plurality of liquid droplets while injecting the disinfectant into the environmental control system.

A fourteenth example includes the system of the thirteenth example, wherein the one or more nozzles are configured to aerosolize the disinfectant into the plurality of liquid droplets having an average diameter less than about 10 micrometers.

A fifteenth example includes the system of any one of the twelfth through fourteenth examples, wherein the disinfectant assembly comprises one or more vaporizers configured to vaporize the disinfectant while injecting the disinfectant into the environmental control system.

A sixteenth example includes the system of any one of the twelfth through fifteenth examples, wherein the disinfectant assembly is part of the environmental control system.

A seventeenth example includes the system of any one of the twelfth through sixteenth examples, wherein the one or more supply air sources comprise at least one of an air conditioner pack or a recirculation fan of the environmental control system.

An eighteenth example includes the system of any one of the twelfth through seventeenth examples, wherein the one or more supply air sources comprises one or more recirculation fans configured to discharge cabin air to the ECS, and wherein the system further comprising one or more filters configured to remove disinfectant from the cabin air.

A nineteenth example includes the system of any one of the twelfth through eighteenth examples, wherein the environmental control system includes a mix manifold configured to receive the supply air from the one or more supply air sources, receive the disinfectant from the disinfectant assembly, and discharge the supply air and the disinfectant to the aircraft cabin.

A twentieth example includes the system of the nineteenth example, including an air distribution system configured to distribute the supply air from the mix manifold to the aircraft cabin to distribute the disinfectant through the cabin and an air discharge system configured to discharge cabin air from the cabin to one or more outflow valves to remove the disinfectant from the cabin.

Various examples have been described. These and other examples are within the scope of the following claims.

What is claimed is:

1. A method of disinfecting an aircraft cabin, comprising:
    vaporizing a non-peroxide disinfectant;
    injecting the vaporized non-peroxide disinfectant into an environmental control system of an aircraft; and
    discharging supply air through the environmental control system to discharge the vaporized non-peroxide disinfectant into the aircraft cabin.

2. The method of claim 1,
    wherein the non-peroxide disinfectant comprises a non-corrosive, non-toxic disinfectant, and
    wherein the non-peroxide disinfectant is discharged into the aircraft cabin in a presence of personnel in the aircraft cabin.

3. The method of claim 1, further comprising discharging the non-peroxide disinfectant from the aircraft cabin using at least one of an outflow valve or a recirculation fan.

4. The method of claim 1, wherein the supply air is discharged through the environmental control system by at least one of an air conditioner pack or a recirculation fan of the environmental control system.

5. The method of claim 1,
    wherein the environmental control system includes a mix manifold, and
    wherein the non-peroxide disinfectant is injected into the mix manifold through a ground port.

6. The method of claim 1, further comprising recirculating air through one or more filters to remove the non-peroxide disinfectant from cabin air from the aircraft cabin.

7. The method of claim 1, further comprising maintaining a constant application of the non-peroxide disinfectant to achieve the required coverage within a setpoint for a duration.

8. A system for disinfecting an aircraft cabin, comprising:
    a disinfectant assembly configured to inject a non-peroxide disinfectant into an environmental control system of an aircraft; and
    one or more supply air sources configured to discharge supply air into the environmental control system to discharge the non-peroxide disinfectant into the aircraft cabin,
    wherein the disinfectant assembly comprises one or more vaporizers configured to vaporize the non-peroxide disinfectant prior to injecting the non-peroxide disinfectant into the environmental control system.

9. The system of claim 8, wherein the disinfectant assembly comprises one or more nozzles configured to aerosolize the non-peroxide disinfectant into a plurality of liquid droplets while injecting the non-peroxide disinfectant into the environmental control system.

10. The system of claim 9, wherein the one or more nozzles are configured to aerosolize the non-peroxide disinfectant into the plurality of liquid droplets having an average diameter between about 100 nanometers and about 100 micrometers.

11. The system of claim 8, wherein the disinfectant assembly is part of the environmental control system.

12. The system of claim 8, wherein the one or more supply air sources comprise at least one of an air conditioner pack or a recirculation fan of the environmental control system.

13. The system of claim 8,
wherein the one or more supply air sources comprises one or more recirculation fans configured to discharge cabin air to the environmental control system, and
wherein the system further comprising one or more filters configured to remove the non-peroxide disinfectant from the cabin air.

14. The system of claim 8, wherein the environmental control system comprises a mix manifold configured to:
receive the supply air from the one or more supply air sources;
receive the non-peroxide disinfectant from the disinfectant assembly; and
discharge the supply air and the non-peroxide disinfectant to the aircraft cabin.

15. The system of claim 14, further comprising:
an air distribution system configured to distribute the supply air from the mix manifold to the aircraft cabin to distribute the non-peroxide disinfectant through the aircraft cabin; and
an air discharge system configured to discharge cabin air from the aircraft cabin to one or more outflow valves to remove the non-peroxide disinfectant from the aircraft cabin.

16. The method of claim 1,
wherein the non-peroxide disinfectant is injected to an airborne concentration to provide sufficient coverage on surfaces of the aircraft cabin to kill greater than 95% of microorganisms, and
wherein the non-peroxide disinfectant is non-corrosive and non-toxic at the airborne concentration.

17. A method of disinfecting an aircraft cabin, comprising:
discharging supply air through a mix manifold of an environmental control system of an aircraft;
injecting a non-peroxide disinfectant into the mix manifold to discharge the disinfectant into the aircraft cabin;
maintaining an airborne concentration of the disinfectant in the aircraft cabin for a duration of time sufficient for the disinfectant to deposit with a sufficient coverage on surfaces of the aircraft cabin to kill greater than 95% of microorganisms, wherein maintaining the airborne concentration comprises reducing a flow rate of the supply air to the aircraft cabin to allow time for the non-peroxide disinfectant to deposit on the surfaces of the aircraft cabin; and
discharging the non-peroxide disinfectant from the aircraft cabin using at least one of an outflow valve or a recirculation fan, wherein discharging the non-peroxide disinfectant from the aircraft cabin comprises increasing the flow rate of the supply air to the aircraft cabin.

18. The method of claim 17,
wherein maintaining the airborne concentration comprises recirculating the supply air through the aircraft cabin; and
wherein discharging the non-peroxide disinfectant from the aircraft cabin further comprises recirculating air through one or more filters to remove the non-peroxide disinfectant from cabin air from the aircraft cabin.

19. The method of claim 17, further comprising vaporizing the non-peroxide disinfectant prior to injecting the non-peroxide disinfectant into the environmental control system.

* * * * *